United States Patent [19]

Dusza et al.

[11] 4,444,774
[45] Apr. 24, 1984

[54] 7-HETEROARYL[1,2,4]TRIAZOLO[1,5-A]PYRIMIDINES

[75] Inventors: John P. Dusza; Jay D. Albright, both of Nanuet, N.Y.

[73] Assignee: American Cyanamid Company, Stamford, Conn.

[21] Appl. No.: 403,185

[22] Filed: Jul. 29, 1982

[51] Int. Cl.³ .............................................. C07D 487/04
[52] U.S. Cl. ..................................... 424/251; 544/263
[58] Field of Search .......................... 544/263; 424/251

[56] References Cited

U.S. PATENT DOCUMENTS 4,209,621  6/1980  Dusza et al. ........................ 544/263
4,281,000  7/1981  Dusza et al. ........................ 544/281

FOREIGN PATENT DOCUMENTS 1148629  4/1969  United Kingdom ................ 544/263

Primary Examiner—Paul M. Coughlan, Jr.
Attorney, Agent, or Firm—Edward A. Conroy, Jr.

[57] ABSTRACT

This disclosure describes 7-heteroaryl[1,2,4]-triazolo[1,5-a]pyrimidines which are useful as anxiolytic agents.

7 Claims, No Drawings

7-HETEROARYL[1,2,4]TRIAZOLO[1,5-A]PYRIMIDINES

BRIEF SUMMARY OF THE INVENTION

This invention relates to new organic compounds and, more particularly, is concerned with novel 7-heteroaryl[1,2,4]triazolo[1,5-a]pyrimidines which may be represented by the following general formula:

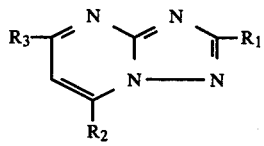

wherein $R_1$ is hydrogen or alkyl having from 1 to 3 carbon atoms; $R_2$ is 3-pyridyl, 3-thienyl or a 2-thienyl moiety of the formula:

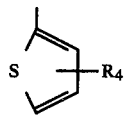

wherein $R_4$ is hydrogen or alkyl having from 1 to 3 carbon atoms; and $R_3$ is hydrogen, methyl or trifluoromethyl. The invention also includes novel compositions of matter containing the above defined compounds which are useful as anxiolytic agents and the method of meliorating anxiety in mammals therewith.

DETAILED DESCRIPTION OF THE INVENTION

The novel compounds of the present invention are generally obtainable as white to pale yellow crystalline solids having characteristic melting point and absorption spectra. The bases are appreciably soluble in solvents such as acetone, ethanol, toluene, carbon tetrachloride, methylene chloride and the like but are relatively insoluble in water. The organic bases of the present invention form non-toxic acid-addition salts with a variety of pharmacologically acceptable organic and inorganic salt forming reagents. Thus, acid-addition salts, formed by admixture of the organic free base with one or two equivalents of an acid, suitably in a netural solvent, are formed with such acids as sulfuric, phosphoric, hydrochloric, hydriodic, sulfamic, citric, lactic, fumaric, succinic, tartaric, acetic, benzoic, gluconic, ascorbic, and the like. The acid-addition salts are relatively insoluble in non-polar organic solvents such as diethyl ether, benzene, toluene, and the like but are appreciably soluble in water. For purposes of this invention, the free bases are equivalent to their non-toxic acid-addition salts.

The novel compounds of the present invention may be readily prepared in accordance with the following reaction scheme:

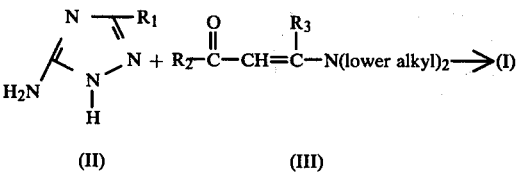

wherein $R_1$, $R_2$ and $R_3$ are as hereinabove defined. In accordance with the above reaction scheme, an appropriately substituted 3-amino-1,2,4-triazole (II) is condensed with an appropriately substituted 3-di(lower alkyl)aminoacrylophenone (III) in an inert organic solvent such as a lower alkanol, dioxane, tetrahydrofuran, toluene and the like, with or without acid catalysis. The preferred procedure is the reaction of (II) with (III) in refluxing glacial acetic acid for 0.5–10 hours to provide the compounds (I) of the invention. Alternatively, the novel compounds of the present invention wherein $R_3$ is methyl or trifluoromethyl may be readily prepared by condensing an appropriately substituted 3-amino-1,2,4-triazole (II) with a 1,3-diketone of the formula:

wherein $R_3$ is methyl or trifluoromethyl and $R_2$ is as hereinabove defined. The preferred procedure is the reaction of (II) with (IV) in refluxing glacial acetic acid for 2–10 hours to provide the compounds (I) of the invention where $R_3$ is methyl or trifluoromethyl.

The 7-heteroaryl[1,2,4]triazolo[1,5-a]pyrimidines (I) of the present invention wherein $R_3$ is hydrogen may be readily prepared by condensing an appropriately substituted 3-amino-1,2,4-triazole (II) with a compound of the formula:

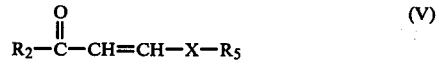

wherein X is oxygen or sulfur; $R_5$ is hydrogen, lower alkyl, an alkali metal (e.g., sodium, potassium or lithium), acetyl or benzoyl. This reaction may be carried out in inert organic solvents such as lower alkanols, dioxane, tetrahydrofuran, toluene and the like with or without acid catalysis. The reaction may be carried out in glacial acetic acid and when $R_5$ is an alkali metal one equivalent of acid is added to give a compound of formula (V) wherein $R_5$ is hydrogen, as an intermediate in the ring closure to the novel compounds of formula (I) wherein $R_3$ is hydrogen.

The novel compounds (I) of the present invention may also be readily prepared by condensing an appropriately substituted 3-amino-1,2,4-triazole (II) with a compound of the formula:

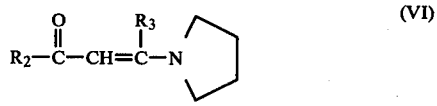

wherein $R_2$ and $R_3$ are as hereinabove defined. The preferred procedure is the reaction of (II) with (VI) in refluxing glacial acetic acid for 2–10 hours.

The novel compounds of the present invention possess central nervous system activity at non-toxic doses and as such are useful as anxiolytic agents. That is they produce certain responses in standard tests with laboratory animals which are known to correlate well with relief of anxiety in man. The compounds have been tested pharmacologically and found to have such properties with a desirable wide spread between doses producing anxiolytic activity and toxic symptoms.

The anti-anxiety properties of the novel compounds of the present invention have been established in a test which indicates anxiolytic activity by the measure of protection from convulsions resulting from the administration of pentylenetetrazole. Single or graded dose levels of the test compounds were administered orally or intraperitoneally in a 2% starch vehicle containing 0.5% v/v polyethylene glycol and one drop of polysorbate 80 or distilled water and one drop of polysorbate 80 to groups of at least 4 rats. At 30 or 60 minutes, the rats were treated intravenously with pentylenetetrazole at a dose of 23 mg./kg. of body weight. This dose is estimated to cause clonic seizures in 99% of unprotected rats. The test compounds are considered active if they protect 50% or more of the rats from clonic seizures. It has been reported [R. T. Hill and D. H. Tedeschi, "Animal Testing and Screening Procedures in Evaluating Psychotropic Drugs" in "An Introduction to Psychopharmacology", Eds. R. R. Rech and K. E. Moore, Raven Press, New York, pp. 237–288 (1971)] that there is a high degree of correlation between antagonism of pentylenetetrazole seizures in rats and anti-anxiety effects in higher warm-blooded animals. The following representative compounds of the present invention have been shown to possess anxiolytic activity when tested as described above:

7-(3-Pyridyl)[1,2,4]triazolo[1,5-a]pyrimidine
7-(3-Thienyl)[1,2,4]triazolo[1,5-a]pyrimidine
2-Methyl-7-(3-pyridinyl)-5-(trifluoromethyl)[1,2,4]triazolo[1,5-a]pyrimidine
2-Ethyl-5-methyl-7-(2-thienyl)[1,2,4]triazolo[1,5-a]pyrimidine.

Another test used to assess anti-anxiety effects is a non-condition passive avoidance procedure described by J. R. Vogel, B. Beer and D. E. Clody, "A Simple and Reliable Conflict Procedure for Testing Anti-Anxiety Agents", Psychopharmacologia, 21, 1–7 (1971). A conflict situation is induced in rats by a modification of this method.

Groups of 8 naive, Wistar strain males rats, weighing 200–240 g. each were deprived of water for 48 hours. The test compounds were administered in single or graded, oral or intraperitoneal doses, suspended in distilled water and one drop of polysorbate 80. Control animals received the vehicle alone. At 30 or 60 minutes each rat was placed in an individual clear plexiglass chamber. Tap water was available ad libitum from a nipple located in a black plexiglass box off the main chamber. A 0.7 milliampere AC shocking current was established between the stainless steel grid floor and the tap. After 20 licks of non-shocked drinking, a 2 second shocking current punishment was administered to the rat. This ratio of 20 licks of non-shocked drinking followed by a 2 second shock penalty was continued for a total of 3 minutes. The number of shocks taken by each rat during the 3 minute interval was recorded and compared to a control group. The test compounds are considered active if the number of shocks received by the test group was significantly higher than the control group by the Mann-Whitney U test. The following representative compounds of the present invention have been shown to possess anxiolytic activity when tested as described above:

7-(3-Pyridyl)[1,2,4]triazolo[1,5-a]pyrimidine
7-(5-Methyl-2-thienyl)[1,2,4]triazolo[1,5-a]pyrimidine.

The active compounds of the present invention are effective for meliorating anxiety in warm-blooded animals when administered in amounts ranging from about 0.1 mg. to about 35.0 mg. per kilogram of body weight per day. A preferred dosage regimen for optimum results would be from about 0.5 mg. to about 20.0 mg. per kilogram of body weight per day, and such dosage units are employed that a total of from about 35 mg. to about 1.4 g. of the active compound for a subject of about 70 g. of body weight are administered in a 24 hour period. This dosage regimen may be adjusted to provide the optimum therapeutic response. For example, several divided doses may be administered daily or the dose be proportionally reduced as indicated by the exigencies of the therapeutic situation. A decided practical advantage is that these active compounds may be administered in any convenient manner such as by the oral, intravenous, intramuscular, or subcutaneous routes.

The active compounds may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, these active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between about 5 and 200 mg. of active compound.

The tablets, troches, pills, capsules and the like may also contain the following: A binder such as gum tragacanth, acacia, corn starch or gelatin, excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts used. In addition, these active compounds may be incorporated into sustained-release preparations and formulations.

These active compounds may also be administered parenterally or intraperitoneally. Solutions or suspensions of these active compounds as a free base or pharmacologically acceptable salt can be prepared in water suitably mixed with surfactant such as hydroxypropylcellulose. Dispersions can also be prepared in glycerol, liquid polyethylene glycols, and mixtures thereof in oils.

Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The invention will be described in greater detail in conjunction with the following specific examples.

EXAMPLE 1

7-(3-Pyridyl)[1,2,4]triazolo[1,5-a]pyrimidine

A mixture of 2.54 g of 3-amino-1,2,4-triazole, 5.29 g of 3-dimethylamino-1-(3-pyridyl)-2-propene-1-one and 25 ml of glacial acetic acid was heated under reflux for 6 hours. The solvent was removed in vacuo and the solid residue was partitioned between a saturated aqueous sodium bicarbonate solution and dichloromethane. The organic layer was separated and dried over powdered anhydrous sodium sulfate. This solution was passed through a short column of a hydrous magnesium silicate and the effluent was refluxed on a steam bath with the gradual addition of hexane until crystallization was noted. On cooling the desired compound was separated and collection by filtration gave 1.95 g. of colorless crystals mp. 209°–210° C.

The following Examples for the preparation of 7-(heteroaryl and substituted heteroaryl)[1,2,4]triazolo-[1,5-a]pyrimidines which are listed in Table I were prepared by the procedure described in Example 1.

TABLE I 7-(Heteroaryl and substituted heteroaryl)[1,2,4]triazolo-[1,5-a]pyrimidines

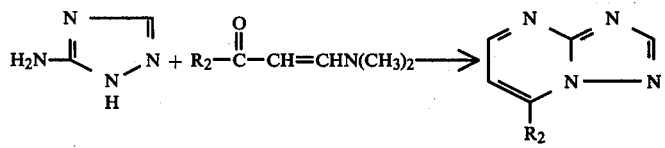

| Example | Compound | R₂ | Description | m.p. °C. |
|---|---|---|---|---|
| 2 | 7-(3-Thienyl)[1,2,4]triazolo-[1,5-a]pyrimidine | 3-thienyl | tan crystals | 146–147 |
| 3 | 7-(2-Thienyl)[1,2,4]triazolo-[1,5-a]pyrimidine | 2-thienyl | pale yellow crystals | 175–176 |
| 4 | 7-(5-Methyl-2-thienyl)[1,2,4,]-triazolo[1,5-a]pyrimidine | (5-methyl-2-thienyl) | light yellow crystals | 150–152 |

EXAMPLE 5

2-Methyl-7-(3-pyridyl)[1,2,4]triazolo[1,5-a]pyrimidine

A reaction mixture of 0.98 g of 3-amino-5-methyl-1,2,4-triazole and 1.76 g of 3-dimethylamino-1-(3-pyridyl)-2-propene-1-one in 25 ml of glacial acetic acid was refluxed for six hours. The procedure was continued as for Example 1 to give 0.85 g of the product of the Example as colorless crystals, mp 244°–245° C.

EXAMPLE 6

2-Methyl-7-(2-thienyl)[1,2,4]triazolo[1,5-a]pyrimidine

By the procedure described in Example 5, 3-amino-5-methyl-1,2,4-triazole was reacted with 3-dimethylamino-1-(2-thienyl)-2-propene-1-one to give 1.05 g of the product of the Example as pale yellow needles, mp 184°–185° C.

EXAMPLE 7

2-Ethyl-7-(3-pyridyl)[1,2,4]triazolo[1,5-a]pyrimidine

A mixture of 1.12 g of 3-amino-5-ethyl-1,2,4-triazole and 1.76 g of 3-dimethylamino-1-(3-pyridyl)-2-propene-1-one in 25 ml of glacial acetic acid was refluxed for six hours and the procedure of Example 1 was continued to give 1.51 g of the desired product as colorless needles, mp 147°–149° C.

The following additional Examples for the preparation of 2-ethyl-7-(heteroaryl and substituted heteroaryl)[1,2,4]triazolo[1,5-a]pyrimidines listed in Table II were prepared by the procedure described in Example 7.

TABLE II

2-Ethyl-7-(heteroaryl and substituted heteroaryl)-[1,2,4]triazolo[1,5-a]pyrimidines

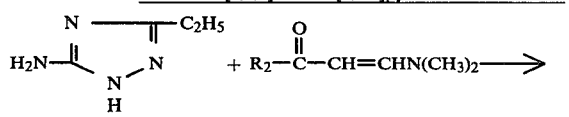

+ 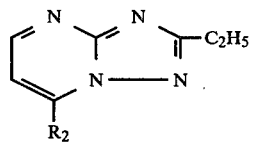 →

[structure]

| Example | Compound | R$_2$ | Description | m.p. °C. |
|---|---|---|---|---|
| 8 | 2-Ethyl-7-(2-thienyl)[1,2,4]-triazolo[1,5-a]pyrimidine | 2-thienyl | pale yellow crystals | 136–137 |
| 9 | 2-Ethyl-7-(3-thienyl)[1,2,4]-triazolo[1,5-a]pyrimidine | 3-thienyl | colorless crystals | 137–138 |
| 10 | 2-Ethyl-7-(5-methyl-2-thienyl9[1,2,4]triazolo-[1,5-a]pyrimidine | (5-methyl-2-thienyl) | tan crystals | 152–153 |

EXAMPLE 11

2-Methyl-7-(3-pyridinyl)-5-(trifluoromethyl)[1,2,4]-triazolo[1,5-a]pyrimidine

A reaction mixture of 0.986 g of 3-amino-5-methyl-1,2,4-triazole and 2.178 g of 4,4,4-trifluoro-1-(3-pyridyl)-1,3-butanedione in 25 ml of glacial acetic acid was refluxed for 4 hours. The mixture was then evaporated to dryness in vacuo and gave a crystalline residue. This residue was partitioned between a saturated aqueous sodium bicarbonate solution and dichloromethane and the procedure of Example 1 was continued to give 1.33 g of the desired product as colorless crystals, mp 195°–197° C.

EXAMPLE 12

7-(2-Thienyl)-5-(trifluoromethyl)[1,2,4,]triazolo[1,5-a]pyrimidine

A mixture of 0.84 g of 3-amino-1,2,4-triazole and 2.22 g of 4,4,4-trifluoro-1-(2-thienyl)1,3-butanedione in 25 ml of glacial acetic acid was heated under reflux for 6 hours. The resulting mixture was worked up as described in Example 11 and gave 1.15 g of the product of the Example as colorless crystals, mp 170°–171° C.

EXAMPLE 13

2-Ethyl-5-methyl-7-(2-thienyl)[1,2,4,]triazolo[1,5-a]pyrimidine

A reaction mixture of 2.21 g of 3-amino-5-ethyl-1,2,4-triazole and 2.21 g of 3-(1-pyrrolidinyl)-1-(2-thienyl)-2-buten-1-one in 25 ml of glacial acetic acid was refluxed for 6 hours. The resulting mixture was worked up as described in Example 11 to give 1.93 g of the desired product as tan crystals, mp 103°–104° C.

EXAMPLE 14

5-Methyl-7-(3-pyridinyl)[1,2,4]triazolo[1,5-a]pyrimidine

A mixture of 0.84 g of 3-amino-1,2,4-triazole and 2.16 g of 3-(1-pyrrolidinyl)-1-(3-pyridyl)-2-buten-1-one in 25 ml of glacial acetic acid was refluxed for 6 hours. The resulting mixture was worked up as described in Example 11 to give 1.12 g of the product of the Example as colorless crystals, mp 183°–185° C.

We claim:

1. A compound selected from the group consisting of those of the formula:

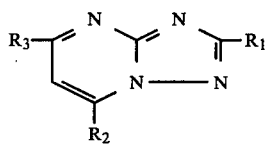

wherein R$_1$ is hydrogen or alkyl having up to 3 carbon atoms; R$_2$ is 3-pyridyl, 3-thienyl or a moiety of the formula:

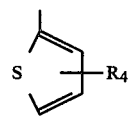

wheren R$_4$ is hydrogen or alkyl having up to 3 carbon atoms; and R$_3$ is hydrogen, methyl or trifluoromethyl; and the pharmacologically acceptable acid-addition salts thereof.

2. The compound in accordance with claim 1; 7-(3-pyridyl)[1,2,4]triazolo[1,5-a]pyrimidine.

3. The compound in accordance with claim 1; 7-(3-thienyl)[1,2,4]triazolo[1,5-a]pyrimidine.

4. The compound in accordance with claim 1; 7-(5-methyl-2-thienyl)[1,2,4]triazolo[1,5-a]pyrimidine.

5. The compound in accordance with claim 1; 2-methyl-7-(3-pyridinyl)-5-(trifluoromethyl)[1,2,4]-triazolo[1,5-a]pyrimidine.

6. The compound in accordance with claim 1; 2-ethyl-5-methyl-7-(2-thienyl)[1,2,4]triazolo[1,5-a]pyrimidine.

7. The method of meliorating anxiety in a warm-blooded animal which comprises administering internally to said warm-blooded animal an effective anti-anxiety amount of a compound of claim 1.

* * * * *